US012673194B2

(12) United States Patent　　(10) Patent No.:　US 12,673,194 B2

Durcan　　(45) Date of Patent:　　Jul. 7, 2026

(54) INTERVENTIONAL SYSTEM HAVING COOPERATIVE BALLOON CATHETER AND GUIDEWIRE

(71) Applicant: ABBOTT CARDIOVASCULAR SYSTEMS INC., Santa Clara, CA (US)

(72) Inventor: Jonathan P. Durcan, Temecula, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 72 days.

(21) Appl. No.: 18/438,347

(22) Filed: Feb. 9, 2024

(65) Prior Publication Data

US 2024/0285920 A1　　Aug. 29, 2024

Related U.S. Application Data

(60) Provisional application No. 63/447,858, filed on Feb. 23, 2023.

(51) Int. Cl.
　　*A61M 29/02*　　(2006.01)
　　*A61M 25/09*　　(2006.01)
　　*A61M 25/10*　　(2013.01)

(52) U.S. Cl.
　　CPC ... *A61M 29/02* (2013.01); *A61M 2025/09083* (2013.01); *A61M 2025/09166* (2013.01);
　　　　　　　　(Continued)

(58) Field of Classification Search
　　CPC ............... A61M 29/02; A61M 25/104; A61M 2025/09083; A61M 2025/09166; A61M 2025/09175; A61M 2029/025; A61M 2025/0183; A61M 2025/09125; A61M 25/09
See application file for complete search history.

(56) References Cited

U.S. PATENT DOCUMENTS 4,616,653　A　*　10/1986　Samson ......... A61M 25/09025
　　　　　　　　　　　　　　　　　　　　　606/192
4,940,062　A　　　7/1990　Hampton et al.
　　　　　　　　　(Continued)

FOREIGN PATENT DOCUMENTS

CA　　　1324052　C　　11/1993
WO　　　9317750　A1　　9/1993

OTHER PUBLICATIONS

PCT International Search Report and Written Opinion from related PCT Application No. PCT/US2024/016032, mailed on Jun. 18, 2024, 18 pages.

*Primary Examiner* — Andrew Restaino
(74) *Attorney, Agent, or Firm* — WOMBLE BODN DICKINSON (US) LLP

(57) ABSTRACT

An interventional system is used to treat a lesion in a target anatomy. The interventional system includes a balloon catheter and a guidewire. The balloon catheter includes a balloon coupled to a catheter shaft. The catheter shaft includes a guidewire lumen having a lumen diameter. The guidewire includes a coil tip coupled to a guidewire shaft at a proximal joint. A coil diameter of the coil tip at the proximal joint is larger than the lumen diameter of the catheter shaft. The interventional system can be used to access and treat the lesion in the target anatomy. Other embodiments are also described and claimed.

20 Claims, 3 Drawing Sheets

(52) U.S. Cl.
CPC . *A61M 2025/09175* (2013.01); *A61M 25/104*
(2013.01); *A61M 2029/025* (2013.01)

(56) References Cited

U.S. PATENT DOCUMENTS

| | | | | |
|---|---|---|---|---|
| 5,045,061 | A * | 9/1991 | Seifert .................. | A61M 25/09 |
| | | | | 600/585 |
| 5,192,295 | A | 3/1993 | Danforth et al. | |
| 5,324,263 | A | 6/1994 | Kraus et al. | |
| 5,465,733 | A * | 11/1995 | Hinohara .............. | A61M 25/09 |
| | | | | 600/585 |
| 8,419,658 | B2 * | 4/2013 | Eskuri .................. | A61M 25/09 |
| | | | | 604/524 |
| 10,722,109 | B2 | 7/2020 | Kermani | |
| 11,420,028 | B2 | 8/2022 | Koike | |
| 2004/0122415 | A1 * | 6/2004 | Johnson ............ | A61M 25/0023 |
| | | | | 604/528 |
| 2004/0193073 | A1 * | 9/2004 | DeMello .............. | A61M 25/09 |
| | | | | 600/585 |
| 2006/0282110 | A1 * | 12/2006 | Litvack ................ | A61M 25/09 |
| | | | | 606/192 |
| 2009/0112126 | A1 * | 4/2009 | Keating ............... | A61M 25/09 |
| | | | | 600/585 |
| 2013/0110001 | A1 * | 5/2013 | Miyata ................. | A61M 25/09 |
| | | | | 600/585 |

\* cited by examiner

INSERT A GUIDEWIRE INTO A TARGET ANATOMY    602

DELIVER A BALLOON CATHETER OVER THE GUIDEWIRE    604

ADVANCE THE GUIDEWIRE AND THE BALLOON CATHETER THROUGH A LESION IN THE TARGET ANATOMY    606

INTERVENTIONAL SYSTEM HAVING COOPERATIVE BALLOON CATHETER AND GUIDEWIRE

This application claims the benefit of priority of U.S. Provisional Patent Application No. 63/447,858, filed on Feb. 23, 2023, titled "INTERVENTIONAL SYSTEM HAVING COOPERATIVE BALLOON CATHETER AND GUIDEWIRE," which is incorporated herein by reference in its entirety to provide continuity of disclosure.

FIELD

The present disclosure relates to medical systems, and more specifically to catheter-based interventional medical systems including medical devices such as balloon dilatation catheters, stent delivery systems, or guidewires.

BACKGROUND

Critical limb ischemia (CLI) involves a severe blockage in a blood vessel of a limb, e.g., a lesion in an artery of a leg, ankle, or foot. The lesion can reduce or stop blood flow to the affected extremity. Patients with CLI often have foot ulcers or gangrene, which results in severe pain. Such patients are also at elevated risk of amputation as a result of the arterial blockages.

A conventional percutaneous transluminal angioplasty (PTA) is a minimally invasive procedure in which a blocked or partially blocked blood vessel in a target anatomy is opened in order to improve blood flow to muscles in the target anatomy. For example, PTA can be used to treat CLI by opening blockages in a blood vessel of a limb. PTA involves advancing a guidewire through a lesion in the blood vessel. A balloon dilatation catheter, having an inflatable balloon on a distal portion thereof, is advanced over the previously introduced guidewire until the balloon of the dilatation catheter is properly positioned across the lesion. When the balloon dilatation catheter is properly positioned, the balloon is inflated to a predetermined size at relatively high pressures to open the lesion and the vascular passageway. The balloon is deflated to allow blood flow to resume through the dilated artery.

SUMMARY

Existing balloon dilatation and guidewire systems may be ineffective at treating CLI by PTA. More particularly, a physician may be able to advance a guidewire through a lesion in an extremity of a patient, however, the lesion may resist passage of a balloon dilatation catheter. The vasculature in the extremity, such as arteries below a knee of the patient, may be too small to pass the balloon dilatation catheter. Furthermore, when a fixed wire balloon catheter is selected for use in treating the lesion, even if the system is able to cross the lesion, access to the blood vessel may be lost when the fixed wire balloon catheter is removed. Loss of access can complicate or prevent performing additional therapies on the lesion. Accordingly an interventional system that allows a guidewire and a balloon catheter to cross a lesion, and facilitates exchange of a subsequent device with the balloon catheter for additional therapies, is needed.

An interventional system is provided. In an embodiment, the interventional system includes a balloon catheter and a guidewire. The balloon catheter includes a balloon coupled to a catheter shaft. The catheter shaft includes a guidewire lumen having a lumen diameter. The guidewire includes a coil tip coupled to a guidewire shaft at a proximal joint. A coil diameter of the coil tip at the proximal joint is larger than the lumen diameter of the catheter shaft.

In an embodiment, a guidewire is provided. The guidewire includes a guidewire shaft, a coil tip, and a proximal joint between the guidewire shaft and the coil tip. The proximal joint includes a proximal face shaped to receive a distal tip of a balloon catheter.

In an embodiment, a method is provided. The method includes delivering a guidewire into a target anatomy. The guidewire includes a coil tip coupled to a guidewire shaft at a proximal joint. The coil tip has a coil diameter at the proximal joint. The method includes delivering a balloon catheter over the guidewire. The balloon catheter includes a balloon coupled to a catheter shaft. The catheter shaft includes a guidewire lumen having a lumen diameter smaller than the coil diameter. The method includes advancing the guidewire and the balloon catheter through a lesion in the target anatomy.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
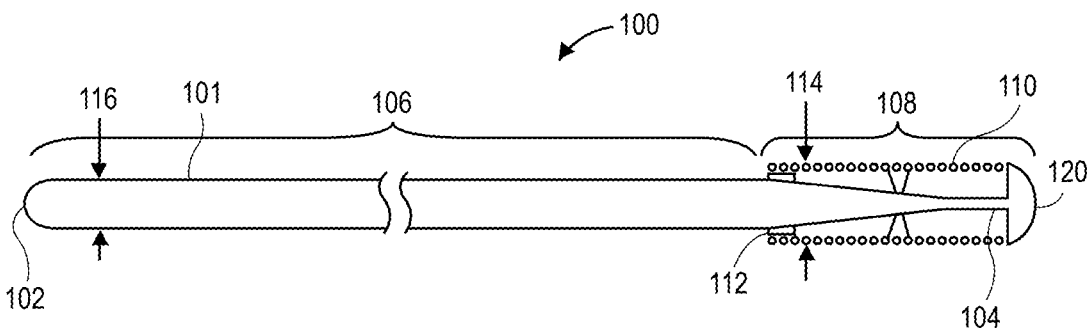
FIG. 1 is a side view of a guidewire, in accordance with an embodiment.

Embodiments describe an interventional system. The interventional system can be used to treat critical limb ischemia (CLI). For example, the interventional system can be used to treat a lesion in an extremity of a patient. Alternatively, the interventional system may be used in other applications, such as to treat lesions in a coronary artery or another peripheral artery. Thus, reference to the system as being used to treat CLI is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a guidewire. Similarly, "proximal" may indicate a second direction opposite to the first direction. Such terms are provided to establish relative frames of reference, however, and are not intended to limit the use or orientation of an interventional system to a specific configuration described in the various embodiments below.

In an aspect, an interventional system includes a balloon catheter and a guidewire. The balloon catheter and the guidewire cooperate to approximate a profile and an overall performance of a fixed wire balloon catheter. More particularly, the guidewire can include a coil tip having a coil diameter at a proximal joint that is larger than a lumen diameter of a guidewire lumen of the balloon catheter. A distal tip of the balloon catheter can be received by the proximal joint. For example, the distal tip can abut and/or lodge against the proximal joint. A crossing profile of the system can therefore be small and the transition between the distal tip and the coil tip can be smooth to allow the system to advance through a lesion in a target anatomy. The balloon catheter can be moved independently from the guidewire. Accordingly, the balloon catheter can be removed from the target anatomy, leaving the guidewire in place to allow an additional therapy device to be tracked over the guidewire through the lesion. Sequentially larger balloons and/or stents may therefore be delivered to and expanded within the lesion to restore blood flow to the extremity.

Referring to FIG. 1, a side view of a guidewire is shown in accordance with an embodiment. A guidewire 100 of an interventional system can minimize a back-end diameter of the supportive wire used for catheter tracking. The guidewire 100 includes a guidewire shaft 101 extending distally from a proximal shaft end 102 to a distal shaft end 104. The guidewire shaft 101 can be segmented into portions having respective features. For example, the guidewire shaft 101 can include a proximal portion 106 extending distally from the proximal shaft end 102 and having a same diameter over a length of the portion. By contrast, a distal portion 108 of the guidewire shaft 101 can extend distally from the proximal portion 106 to the distal shaft end 104 and may have a varying diameter over a length of the portion. The guidewire portions are described in further detail below.

In an embodiment, the guidewire 100 includes a coil tip 110 connected to the guidewire shaft 101. For example, the coil tip 110 can be mounted on and bonded to the guidewire shaft 101 using a thermal or adhesive bond. More particularly, a proximal joint 112 may connect the coil tip 110 to the guidewire shaft 101. The proximal joint 112 can include a solder joint between the coil tip 110 and the guidewire shaft 101, a marker band joined to the coil tip 110 and the guidewire shaft 101 or another interconnection between the coil tip 110 and the guidewire shaft 101. The proximal joint 112 can define a transition point between the proximal portion 106 and the distal portion 108 of the guidewire 100. More particularly, as described below, the proximal joint 112 can interconnect the coil tip 110 and the guidewire shaft 101 in such a manner that a coil diameter 114 of the coil tip 110 at the proximal joint 112 is larger than a shaft diameter 116 of the guidewire shaft 101.

In an embodiment, the coil diameter 114 of the coil tip 110 over the distal portion 108 of the guidewire shaft 101 can be greater than 0.010 inch, e.g., 0.014 inch. The coil tip 110 can have a length of 2 to 10 cm, e.g., 5 cm. Thus, the coil tip 110 can provide a supportive profile to engage and cross a lesion. Guidewire visibility and lesion crossing can also be facilitated by an atraumatic tip 120 mounted on the distal portion 108 of the guidewire shaft 101. The catheter tip 120 can be formed from a radiopaque material and can be rounded, e.g., have a dome profile, to facilitate lesion engagement and crossing.

The coil tip 110 may have a tapered profile. For example, at least a portion of the coil tip 110, e.g., a distal 1-2 cm length of the coil tip 110, may taper from a first coil diameter to a second coil diameter. The first coil diameter may be, e.g., 0.014 inch, as described above. The tapering tip may gradually reduce over the distal length of the coil tip 110 to a smaller tip diameter. For example, the second coil diameter adjacent to or at the atraumatic tip 120 may be in a range of 0.009 to 0.010 inch, e.g., 0.0095 inch.

The coil tip 110 can have a coil configuration to facilitate visibility and tracking through a lesion. For example, a distal length of the coil tip 110, e.g., a distal 3 cm of the coil tip, can be formed from a radiopaque material to enhance visibility of the coil tip 110 under fluoroscopy. A proximal length of the coil tip 110, proximal to the distal length, can be a proximal coil having a diameter equivalent to the proximal diameter of the distal tip coil. The coil tip 110 can have high tip loads, multi-filar coil wires for enhanced torque transmission, or other features that enhance tracking of the guidewire 100 through tight lesions in a target anatomy.

In contrast to the coil tip 110, the shaft diameter 116 of the distal portion 108 of the guidewire shaft 101 can be equal to or less than 0.010 inch. More particularly, a profile of the guidewire 100 can abruptly step down from the coil diameter 114 at the proximal joint 112, e.g., 0.014 inch, to a smaller shaft diameter 116, e.g., 0.010 inch. The shaft diameter 116 can be constant over the proximal portion 106 of the guidewire shaft 101 between the proximal joint 112 and the proximal shaft end 102. Accordingly, the entire length of the proximal portion 106 of a guidewire shaft 101 can have a smaller diameter than the coil tip 110. It will be appreciated that the guidewire shaft dimensions described above may be atypically small for a guidewire shaft 101. The cooperation of the guidewire 100 with a balloon catheter as described below however, can facilitate effective tracking of an interventional system.

Figure 2:
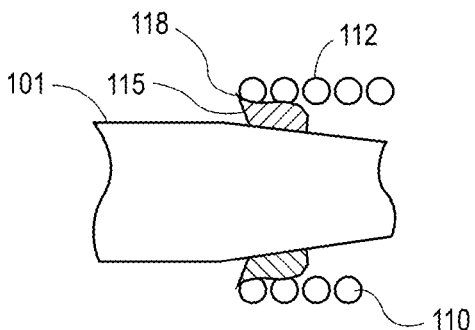
FIG. 2 is a detailed view of proximal joint of a guidewire, in accordance with an embodiment.

Referring to FIG. 2, a detailed view of proximal joint of a guidewire is shown in accordance with an embodiment. The transition between the guidewire shaft 101 and the coil tip 110 at the proximal joint 112 can be abrupt. In an embodiment, the proximal joint 112 is formed with solder. More particularly, a solder joint is formed in a space between the coil tip 110 and the guidewire shaft 101. Alternatively, the proximal joint 112 can include a marker band (FIG. 3) between the guidewire shaft 101 and the coil tip 110 at the proximal joint 112. In any case, the proximal joint 112 can include a proximal face 115 that provides the abrupt transition between the shaft diameter 116 and the coil diameter 114.

In an embodiment, the proximal face 115 is shaped to interfere with a distal tip of a balloon catheter. For example, the proximal face 115 can extend radially outward along a transverse plane (transverse to a longitudinal axis of the guidewire shaft 101) from the guidewire shaft 101 to the coil tip 110. Optionally, the proximal face 115 may be shaped to receive the distal tip of the balloon catheter. More particularly, the proximal face 115 can be shaped to receive the distal tip of the balloon catheter described below with respect to FIGS. 4-5. For example, the proximal face 115 can be tapered radially inward from an outer face edge 118 to the guidewire shaft 101. The inward taper in a distal direction can allow a catheter tip to wedge into the space located vertically between the proximal face 115 and an outer surface of the guidewire shaft 101. Wedging the catheter tip into the tapered space between the proximal joint 112 and the guidewire shaft 101 can create a smooth transition between the coil tip 110 and the catheter. The catheter tip wedged into the chamfer in the proximal joint 112 can also be used to secure the catheter tip against the guidewire shaft 101 to facilitate forcing the system forward through a tight lesion. Accordingly, the presence of a chamfer in the proximal joint 112 to receive the catheter tip can facilitate pushability and tracking of the system.

A tapered proximal face 115 of the proximal joint 112 may be formed in several manners. For example, a solder joint may be formed and the proximal face 115 of the solder joint can be shaped in a grinding process to introduce the inward taper. Alternatively, a chill block can be placed around the guidewire shaft 101 at the location adjacent to the coil tip 110 such that solder can be flowed into the space between the coil tip 110 and the guidewire shaft 101 against the chill block. When the chill block is removed, the abrupt transition of the proximal face 115 can be revealed.

Figure 3:
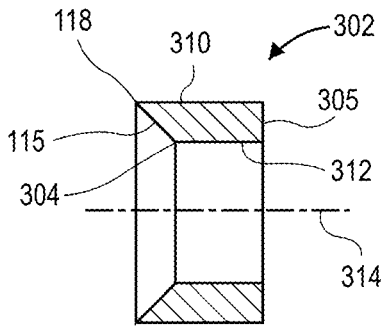
FIG. 3 is a sectional view of a joint component of a guidewire, in accordance with an embodiment.

Referring to FIG. 3, a sectional view of a joint component of a guidewire is shown in accordance with an embodiment. In an embodiment, the proximal joint 112 can be solder formed as shown in FIG. 2. Alternatively, the proximal joint 112 can include a marker band 302 having the proximal face 115. The proximal face 115 may, for example, be a chamfered surface formed in an annular ring of the marker band 302. A countersink tool can be plunged into a central channel of the annular ring to remove a portion of the ring and create the inward tapered surface. More particularly, the proximal face 115 can taper radially inward from the outer face edge 118 to an inner face edge 304 nearer to a central axis 314 of the annular ring. An outer surface 310 and an inner surface 312 of the annular ring may be cylindrical and parallel to each other. The outer surface 310 and inner surface 312 can extend distally from respective edges 118, 304 to a distal face 305. The distal face 305 may be a flat face extending along a plane orthogonal to the central axis 314.

A guidewire manufacturing process can include placing the marker band 302 over the guidewire shaft 101. The coil tip 110 may then be abutted next to the distal face 305 of the marker band 302. For example, a proximal turn of the coil can be located at the distal face 305. By contrast, the inner face edge 304 of the marker band 302 can be located at a location where the proximal portion 106 of the guidewire shaft 101 transitions into the distal portion 108 of the guidewire shaft 101. The assembled components can be bonded to each other, e.g., by solder, to fix the components in place relative to each other.

Figures 4, 5:
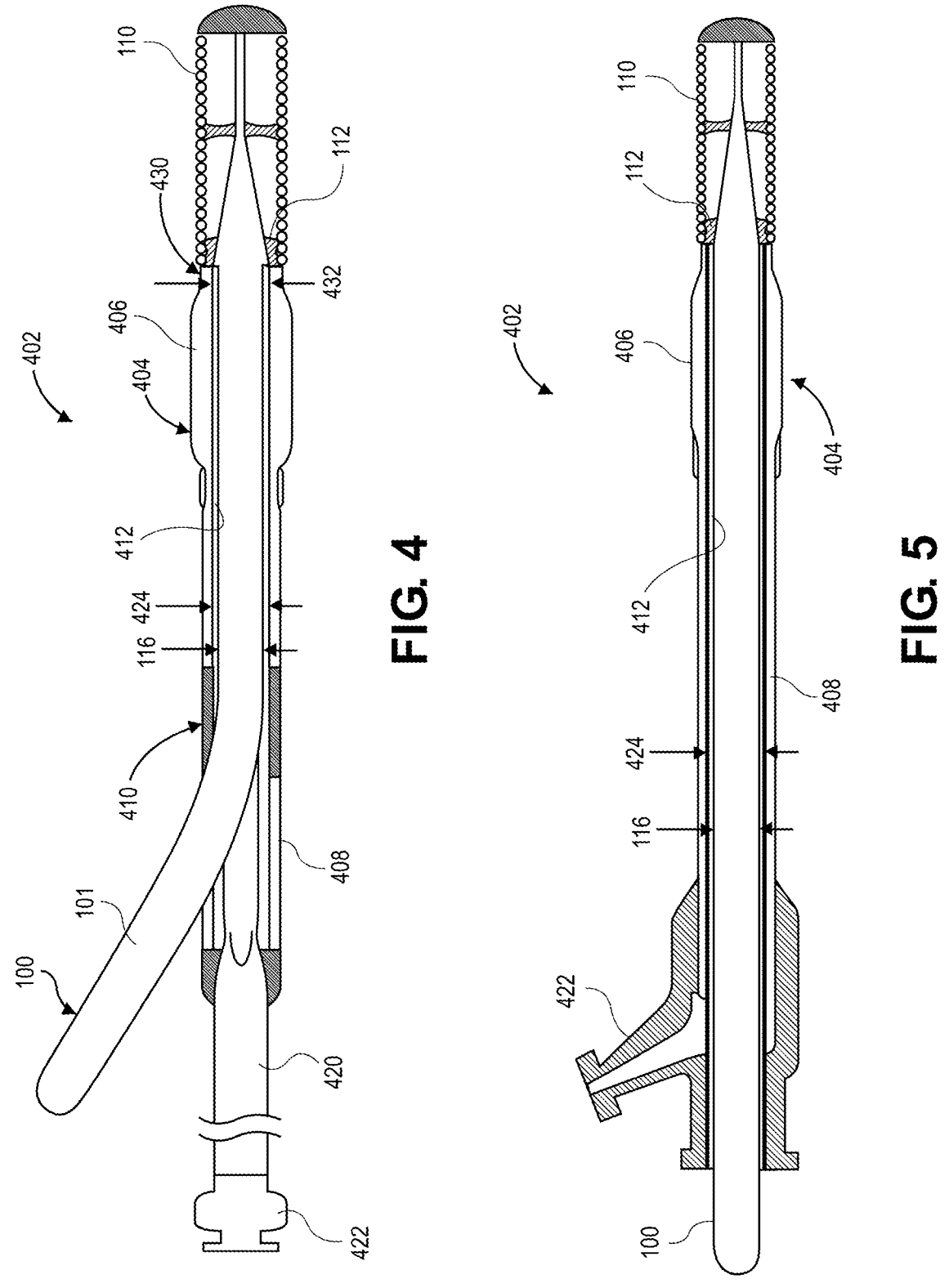
FIG. 4 is a cross-sectional view of an interventional system, in accordance with an embodiment.
FIG. 5 is a cross-sectional view of an interventional system, in accordance with an embodiment.

Referring to FIG. 4, a cross-sectional view of an interventional system is shown in accordance with an embodiment. An interventional system 402 can include the guidewire 100, and a balloon catheter 404. The balloon catheter 404 can have a rapid exchange configuration. More particularly, the balloon catheter 404 can include a balloon 406 mounted on and/or connected to a catheter shaft 408, and the catheter shaft can include a rapid exchange notch 410 to allow the guidewire 100 to pass radially outward through the catheter shaft 408 from a guidewire lumen 412 to a surrounding environment. A hypotube 420 can extend proximally from the portion of the catheter shaft 408 having the rapid exchange notch 410 to a luer hub 422. Inflation fluid can be delivered through the luer hub 422 and the hypotube 420 into the catheter shaft 408. The fluid can transfer distally into the balloon to inflate the balloon 406. Accordingly, the balloon catheter 404 can be used to dilate a target lesion.

The balloon catheter 404 can be sized to provide a low-profile platform for accessing and treating a lesion. In an embodiment, the balloon 406 is a low-profile balloon having an outer diameter that approximates the coil diameter 114. To approximate the coil diameter 114, the catheter shaft profile can be minimized. For example, the guidewire lumen 412 of the catheter shaft 408 can have a lumen diameter 424 that is about a same size as the guidewire shaft 101. More particularly, the lumen diameter 424 may be equal to or less than 0.011 inch. It is noted that such a lumen diameter 424 is comparatively smaller than, e.g., typically-sized 0.0155 inch catheter lumen diameters. As described above, the shaft diameter 116 can be equal to or less than 0.010 inch, and thus, the lumen diameter 424 and the shaft diameter 116 may be equal or approximately equal, e.g., within 0.001 inch of each other. In an embodiment, a wall thickness of the catheter shaft 408 and/or the balloon 406 can be approximately the same as a thickness of the coil tip 110. Accordingly, at least a portion of the balloon catheter 404, e.g., the balloon 406, can have a same outer dimension as the coil tip 110, e.g., 0.014 inch. It will be appreciated that such profile is comparatively low in relation to typical catheter crossing profiles.

The outer dimension of the guidewire shaft 101 can be equal to or slightly smaller than the inner dimension of the guidewire lumen 412. Thus, a coil diameter 114 of the coil tip 110 at the proximal joint 112, which is larger than the shaft diameter 116 of the guidewire shaft 101, may also be larger than the lumen diameter 424 of the catheter shaft 408.

A distal tip 430 of the balloon catheter 404 may advance over the guidewire 100 to the proximal joint 112 without sliding over the coil tip 110. More particularly, the balloon catheter 404 includes the distal tip 430, which can slide over the guidewire shaft 101 to wedge against the proximal joint 112. For example, the distal tip 430 can wedge into the tapered gap formed between the guidewire shaft 101 and the proximal face 115. An outer dimension of the distal tip 430 can be equal to the coil diameter 114. Accordingly, the balloon catheter 404 may work in conjunction with the guidewire 100 to provide an outer profile that is small and continuous over the distal portion 108 of the interventional system 402.

A tip inner diameter 432 of the distal tip 430 can be equal to or less than the shaft diameter 116. When the tip inner diameter 432 is slightly less than the shaft diameter 116, e.g., 0.0002 inch less, then the distal tip 430 can slide in a friction fit over the guidewire shaft 101. The distal tip 430 can therefore engage the proximal joint 112 and be retained in position by friction between the components. More particularly, the components of the interventional system 402 can bind with each other to allow the balloon catheter 404 and the guidewire 100 to be tracked through a target anatomy in unison. The bound components can essentially function like a fixed wire system. Removal of the balloon catheter 404 from the guidewire 100 may nonetheless be achieved by retracting the balloon catheter 404 while holding the guidewire 100 in place.

The components of the interventional system 402 may be sized in a slip fit, rather than a friction fit. More particularly, the guidewire lumen diameter and the tip inner diameter may be slightly larger than the shaft diameter 116. The balloon catheter 404 may more easily slide over the guidewire 100 in such case. In an embodiment, to allow the components to be tracked together, a clip (not shown) may be used to secure the guidewire 100 to the hypotube 420. The clip can be mounted over the guidewire 100 and/or the balloon catheter 404 to clamp the components together. More particularly, the clip can lock the components together to allow the components to be moved synchronously. Alternatively or additionally, a user may hold the guidewire 100 and the hypotube 420 together while advancing the components into the anatomy.

Referring to FIG. 5, a cross-sectional view of an interventional system is shown in accordance with an embodiment. The balloon catheter 404 of the interventional system 402 can have an over-the-wire catheter configuration. The balloon catheter 404 having the over-the-wire catheter configuration can incorporate features similar to those described above with respect to FIG. 4. More particularly, the balloon catheter 404 can have components, such as the balloon 406, the catheter shaft 408 including the guidewire lumen 412 having the lumen diameter 424, etc. Such components may interact with the guidewire 100 as described above.

The over-the-wire system can also include the catheter shaft 408 extending proximally from the balloon 406 to the luer hub 422. In contrast to the rapid exchange configuration, the over-the-wire configuration may have the luer hub 422 that includes a side port for delivering inflation fluid through the catheter shaft 408 to the balloon 406. The luer hub 422 may also include a guidewire port to receive the guidewire 100, e.g., to track the balloon catheter 404 over the guidewire 100. The interaction between the components of the rapid exchange system and the over-the-wire system will be understood by one skilled in the art by inspection of FIGS. 4-5.

Figure 6:
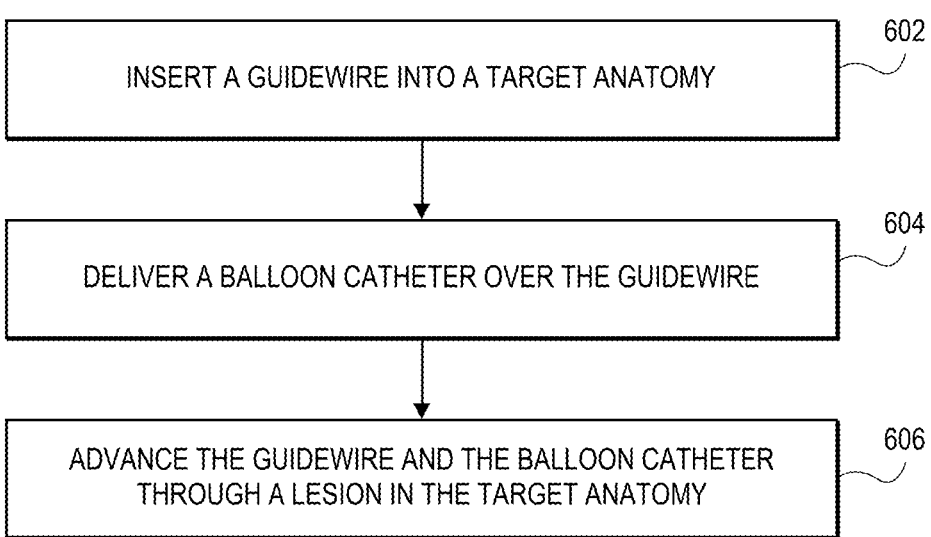
FIG. 6 is a flowchart of a method of using an interventional system to treat a lesion in a target anatomy, in accordance with an embodiment.

Referring to FIG. 6, a flowchart of a method of using an interventional system to treat a lesion in a target anatomy is shown in accordance with an embodiment. At operation 602, the guidewire 100 is delivered into a target anatomy. For example, the guidewire 100 can be tracked into a blood vessel of a limb, such as an artery in a foot. The coil tip 110 of the guidewire 100 can engage a lesion in the target anatomy.

At operation 604, the balloon catheter 404 is delivered over the guidewire 100. The balloon catheter 404 can be advanced over the guidewire shaft 101. The distal tip 430 of the balloon catheter 404 can contact the proximal joint 112. For example, the distal tip 430 can wedge into the tapered space defined by the proximal face 115 of the proximal joint 112. When the distal tip 430 is wedged against the proximal face 115, the inner surface of the distal tip 430 can be secured against the outer surface of the guidewire shaft 101. More particularly, the surfaces can have a friction fit to cause the balloon catheter 404 and the guidewire 100 to cooperate or the catheter can be held in place on the guidewire 100. A stiffness profile of the interventional system 402 can be similar to a fixed wire system when the guidewire 100 and the balloon catheter 404 are in cooperation. More particularly, a crossing profile and an overall support profile of the system may emulate a fixed wire system or a guidewire typically used to treat CLI.

At operation 606, the guidewire 100 and the balloon catheter 404 may be synchronously advanced through the lesion in the target anatomy. The crossing profile and the combined stiffness of the guidewire 100 and the balloon catheter 404 can advance through the lesion to allow the balloon 406 to be located within the lesion. The balloon 406 may be inflated to dilate the lesion. Accordingly, the interventional system 402 can treat the lesion.

In contrast to a fixed wire system, the balloon catheter 404 may be removed from the guidewire 100. More particularly, the balloon catheter 404 can be tugged while holding the guidewire 100 in place to retract the balloon catheter 404 from the guidewire 100. A second device, e.g., a secondary balloon catheter and/or stent delivery system may be tracked over the guidewire 100 to treat the lesion in the target anatomy.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. An interventional system, comprising:
   a balloon catheter including a balloon coupled to a catheter shaft, wherein the catheter shaft includes a guidewire lumen having a lumen diameter; and
   a guidewire removable from the balloon catheter and including a coil tip coupled to a guidewire shaft at a proximal joint, wherein a coil diameter of the coil tip at the proximal joint is larger than the lumen diameter of the catheter shaft, and wherein the proximal joint is radially between the coil tip and the guidewire shaft and includes a proximal face tapering radially inward in a distal direction from the coil tip to the guidewire shaft.

2. The interventional system of claim 1, wherein the guidewire shaft has a shaft diameter that is constant between the proximal joint and a proximal shaft end.

3. The interventional system of claim 2, wherein the balloon catheter includes a distal tip having a tip inner diameter equal to or less than the shaft diameter.

4. The interventional system of claim 3, wherein the tip inner diameter is less than the lumen diameter.

5. The interventional system of claim 4, wherein the lumen diameter is equal to or less than 0.011 inch.

6. The interventional system of claim 2, wherein the shaft diameter is equal to or less than 0.010 inch.

7. The interventional system of claim 1, wherein the proximal face is shaped to receive a distal tip of the balloon catheter.

8. The interventional system of claim 7, wherein the proximal face is tapered radially inward from an outer face edge to the guidewire shaft.

9. The interventional system of claim 7, wherein the proximal joint includes a marker band between the guidewire shaft and the coil tip, and wherein the proximal face is on the marker band.

9

10. A guidewire, comprising:
a guidewire shaft;
a coil tip; and
a proximal joint radially between the guidewire shaft and the coil tip, wherein the proximal joint includes a proximal face shaped to receive a distal tip of a balloon catheter, and wherein the proximal face tapers radially inward in a distal direction from the coil tip to the guidewire shaft.

11. The guidewire of claim 10, wherein the guidewire shaft has a shaft diameter that is constant between the proximal joint and a proximal shaft end.

12. The guidewire of claim 10, wherein the proximal face is tapered radially inward from an outer face edge to the guidewire shaft.

13. The guidewire of claim 10, wherein the proximal joint includes a marker band between the guidewire shaft and the coil tip, and wherein the proximal face is on the marker band.

14. A method, comprising:
delivering a guidewire into a target anatomy, wherein the guidewire includes a coil tip coupled to a guidewire shaft at a proximal joint, and wherein the coil tip has a coil diameter at the proximal joint, and wherein the proximal joint is radially between the coil tip and the guidewire shaft and includes a proximal face tapering radially inward in a distal direction from the coil tip to the guidewire shaft;

delivering a balloon catheter over the guidewire, wherein the balloon catheter is removably disposed on the guidewire, wherein the balloon catheter includes a balloon coupled to a catheter shaft, and wherein the catheter shaft includes a guidewire lumen having a lumen diameter smaller than the coil diameter; and
advancing the guidewire and the balloon catheter through a lesion in the target anatomy.

15. The method of claim 14, wherein the guidewire shaft has a shaft diameter that is constant between the proximal joint and a proximal shaft end.

16. The method of claim 15, wherein the balloon catheter includes a distal tip having a tip inner diameter equal to or less than the shaft diameter.

17. The method of claim 16, wherein the tip inner diameter is less than the lumen diameter.

18. The method of claim 14, wherein the proximal face is shaped to receive a distal tip of the balloon catheter.

19. The method of claim 18, wherein the proximal face is tapered radially inward from an outer face edge to the guidewire shaft.

20. The method of claim 18, wherein the proximal joint includes a marker band between the guidewire shaft and the coil tip, and wherein the proximal face is on the marker band.

* * * * *